(12) United States Patent
Hori

(10) Patent No.: US 6,909,286 B2
(45) Date of Patent: Jun. 21, 2005

(54) METHOD OF INSPECTING INSULATORS TO DETECT DEFECTS INCLUDING MEASURING LEAKAGE CURRENT FLOWING THROUGH THE INSULATOR

(75) Inventor: Koji Hori, Kuwana (JP)

(73) Assignee: Denso Corporation (JP)

( * ) Notice: Subject to any disclaimer, the term of this patent is extended or adjusted under 35 U.S.C. 154(b) by 0 days.

(21) Appl. No.: 10/660,665

(22) Filed: Sep. 12, 2003

(65) Prior Publication Data
US 2004/0051537 A1 Mar. 18, 2004

(30) Foreign Application Priority Data
Sep. 13, 2002 (JP) ........................................ 2002-268575

(51) Int. Cl.[7] .............................................. F02P 17/00
(52) U.S. Cl. ........................................ 324/401; 324/536
(58) Field of Search ................................ 324/399, 400, 324/401, 551, 536; 382/149

(56) References Cited

U.S. PATENT DOCUMENTS

| | | | | |
|---|---|---|---|---|
| 2,175,038 A | * | 10/1939 | Soper | ........................ 324/400 |
| 2,685,060 A | * | 7/1954 | Wampole et al. | ........... 324/401 |
| 2,801,384 A | * | 7/1957 | Pierce | ........................ 324/401 |
| 2,913,659 A | * | 11/1959 | Whaley | ....................... 324/401 |
| 3,330,718 A | * | 7/1967 | James, Jr. et al. | ........... 156/554 |
| 3,775,686 A | * | 11/1973 | Ganger et al. | .............. 324/546 |
| 5,254,954 A | * | 10/1993 | Fujimoto et al. | ........... 324/551 |
| 6,426,626 B1 | * | 7/2002 | Kravis | ........................ 324/388 |

* cited by examiner

*Primary Examiner*—Anjan Deb
*Assistant Examiner*—Walter Benson
(74) *Attorney, Agent, or Firm*—Nixon & Vanderhye PC

(57) ABSTRACT

A method of inspecting insulators such as spark plug insulators for defects, whereby a plurality of insulators are inspected concurrently by being disposed with a plurality of first electrodes engaged in respective apertures in the insulators, and with apertures formed in a second electrode being disposed to peripherally enclose respective insulators. With the insulators and electrodes set in a closed chamber under high air pressure, and high voltage applied between the first and second electrodes, any defect is detected based on a level of leakage current which then flows.

6 Claims, 4 Drawing Sheets

METHOD OF INSPECTING INSULATORS TO DETECT DEFECTS INCLUDING MEASURING LEAKAGE CURRENT FLOWING THROUGH THE INSULATOR

BACKGROUND OF THE INVENTION

1. Field of Application

The present invention relates to a method of inspecting insulators to detect defects. The term "insulator" as used herein, unless otherwise indicated, signifies a solid electrically insulating member, such as the insulator portion of a spark plug of an internal combustion engine. It is assumed in the following that each insulator which is to be inspected has an aperture formed therein, such as the central aperture which extends axially through a spark plug insulator.

2. Description of Prior Art

A prior art method of insulator defect detection is known whereby a first electrode which is needle-shaped is inserted into a central aperture of an insulator such as a spark plug insulators, and a second electrode which is also needle-shaped is disposed at a distance from the second electrode such that a spark discharge can occur between the first and second electrodes. A high voltage is then applied between the first and second electrodes while the insulator is being rotated, so that repetitive spark discharges occur between the first and second electrodes. When this occurs, a judgement is made as to whether or not the insulator is defective, based upon whether or not the spark discharges take place along a predetermined path.

That is to say, if there is no defect in the insulator, then the spark discharges between the tips of the first and second electrodes will occur normally, whereas if the insulator is defective, then the current flow of the discharge will pass through the defective portion of the insulator. Thus, it is possible to determine whether or not the insulator is defective, by observing the path taken by the spark discharges.

With such a method it is essential to ensure that the spark discharges will occur along predetermined paths, between the tips of the first and second electrodes. However when a high value of potential difference is established between the first and second electrodes for producing such spark discharges, if the potential difference is excessively high then the discharges may occur along other paths, i.e., passing through metal portions of the inspection apparatus. For that reason, there are limitations on the values of high voltage which can be used in such an inspection method. Hence, it is difficult to ensure that insulators can be tested for providing a very high degree of electrical insulation.

Furthermore with such a insulator defect inspection method, since each of the first and second electrodes is formed with a needle configuration in order to generate spark discharges, it is necessary to rotate the insulator with respect to the second (i.e., external) electrode in order to inspect the entire periphery of the insulator. Hence it is necessary to provide a motor-driven apparatus for rotating each insulator that is to be inspected, while spark discharges repetitively occur around the periphery of the insulator. That is to say even if a large batch of insulators are to be inspected, it is necessary to use such an apparatus (or plurality of apparatuses) to individually rotate each of the insulators. This is a basic disadvantage of such a prior art insulator defect inspection method.

Furthermore, due to the fact that the tip of the first electrode is located at one specific position within the aperture in the insulator that is being inspected, and any by-passing of the spark discharges (due to current flowing through a defect region in the insulator) will take place along a path between the respective tips of the first and second electrodes, the range of positions in the insulator which are effectively inspected by such a method is limited.

SUMMARY OF THE INVENTION

It is an objective of the present invention to overcome the problems of the prior art set out above, by providing an insulator defect inspection method whereby insulators can be effectively inspected to ensure that they provide a high degree of electrical insulation.

It is a further objective to provide an insulator defect inspection method whereby it is not necessary for an insulator defect inspection apparatus to be provided with a rotation apparatus for individually rotating each of respective insulators which are to be inspected.

It is a further objective to provide an insulator defect inspection method whereby a wide range of positions in an insulator can be effectively inspected for defects.

To achieve the above objectives, according to a first aspect the invention provides an insulator defect inspection method whereby each insulator (i.e., having an aperture formed therein) that is to be inspected is placed in a pressure-proof chamber, with a first electrode inserted into the aperture of the insulator and with a second electrode disposed at the exterior of the insulator. The pressure-proof chamber is filled with air under a pressure which is higher than atmospheric pressure, a high potential difference is established between the first and second electrodes, and the level of leakage current which flows between the first and second electrodes is measured. If the leakage current exceeds a predetermined value, then the insulator is judged to be defective, while otherwise it is judged to be a satisfactory product.

In that way, since the pressure-proof chamber is filled with air under a pressure that is above atmospheric pressure, a high value of voltage can be applied between the first and second electrodes without occurrence of spark discharges. By using such a high value of voltage, it becomes possible to reliably test insulators for having a very high degree of insulation, by measurement of the level of leakage current that flows between the first and second electrodes.

According to a second aspect, the insulator is inserted into a cavity formed in the second electrode, with the second electrode being formed of metal plate. In that way, defect detection can be applied to a region of the insulator which extends over a wide range, i.e., with it being possible to increase that range by as required, by increasing the thickness of the metal plate that is used to form the second electrode, so that a correspondingly larger peripheral area of the insulator is enclosed by the aperture in the second electrode. Hence, a substantially greater range of positions on the insulator are inspected for defects with such a method than is possible with prior art methods such as that described above.

According to a third aspect, the second electrode is shaped and positioned such as to enclose the periphery of the insulator which is being tested. That is to say, the second electrode is disposed such as to closely surround a region of the outer surface of the insulator that extends continuously around the periphery of the insulator. As a result, it is unnecessary to rotate the insulator which is being inspected, in order to examine the entire periphery of the insulator, so that it becomes unnecessary to provide a rotation apparatus for that purpose.

According to a fourth aspect, such a method of insulator defect inspection can be used in a batch inspection process, i.e., can be applied to concurrently inspect a plurality of insulators, with a single second electrode (i.e., having a plurality of apertures for accommodating the insulators) and a plurality of first electrodes being provided in correspondence with the respective insulators. A high value of voltage is applied between the second electrode and each of the plurality of first electrodes, and it is judged that there is a defect in at least one of the plurality of insulators if a level of leakage current which flows between the first and second electrodes exceeds a predetermined value, while otherwise it is judged that the entire batch of insulators is satisfactory. In that way, an entire batch of insulators can be inspected concurrently by single operation.

According to a fifth aspect, such concurrent batch defect inspection is performed with the plurality of first electrodes, the plurality of insulators and the second electrode being enclosed within a pressure-proof chamber, filed with air under a pressure which is higher than atmospheric pressure. If the leakage current exceeds the predetermined value, then that batch of insulators is subjected to individual unit sorting inspection, so that the defective insulator or insulators can be removed from the batch.

In that way, the advantage of concurrent batch defect inspection is achieved while ensuring that if a defective insulator should occur, it will be reliably detected.

According to a sixth aspect, when such a process of individual unit sorting inspection has been applied to all of a batch of insulators for which a defect was detected by the concurrent batch defect inspection operation, then all of the insulators which have been found free from defect by the individual unit sorting inspection operation are then again subjected to the concurrent batch defect inspection operation. This ensures further reliability of the inspection process.

Preferably, the pressure-proof chamber is filled with dry air (preferably having a dew point of −20 degrees C. or less), under the aforementioned high pressure, to thereby suppress spark discharges and so enable the insulators to be tested for having a very high degree of insulation.

DESCRIPTION OF PREFERRED EMBODIMENTS

Figure 1:
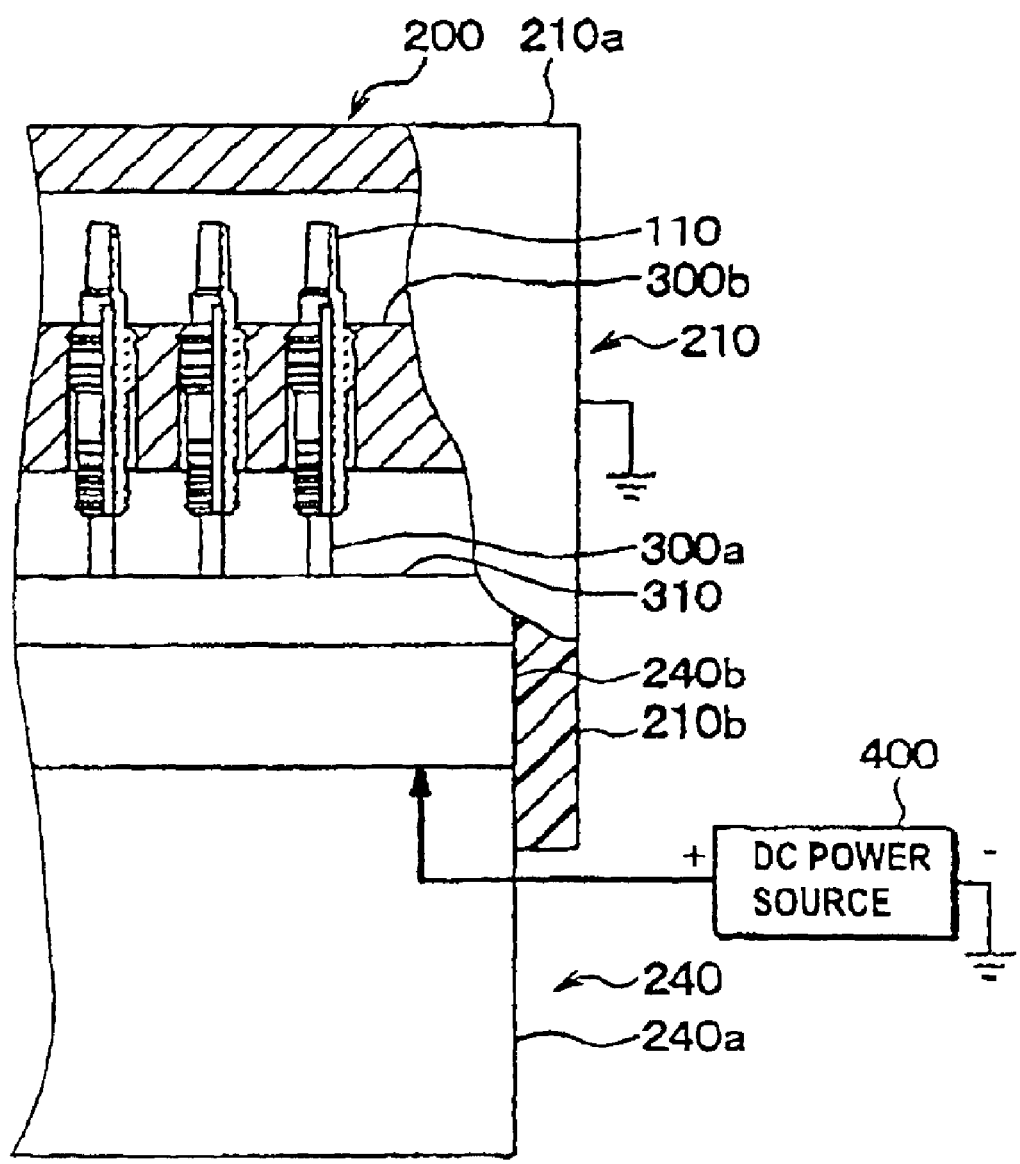
FIG. 1 is a partial diagram of an apparatus for performing concurrent inspection of a plurality of insulators for defects by detection of leakage current.

A first embodiment will be described referring to FIG. 1. This embodiment is applicable to the inspection of spark plugs for use in an internal combustion engine. A plurality of insulators are inspected as a single batch, concurrently, in a single inspection operation. In FIG. 1, the cross-hatched regions indicate cross-sectional areas. The inspection is performed within the interior of a pressure-proof chamber 200, which is filled with air under a higher pressure than atmospheric pressure. The pressure-proof chamber 200 is formed of a supporting portion 240 in conjunction with an upper movable portion 210, which can be raised and lowered by a slide mechanism (not shown in the drawings).

Figure 2:
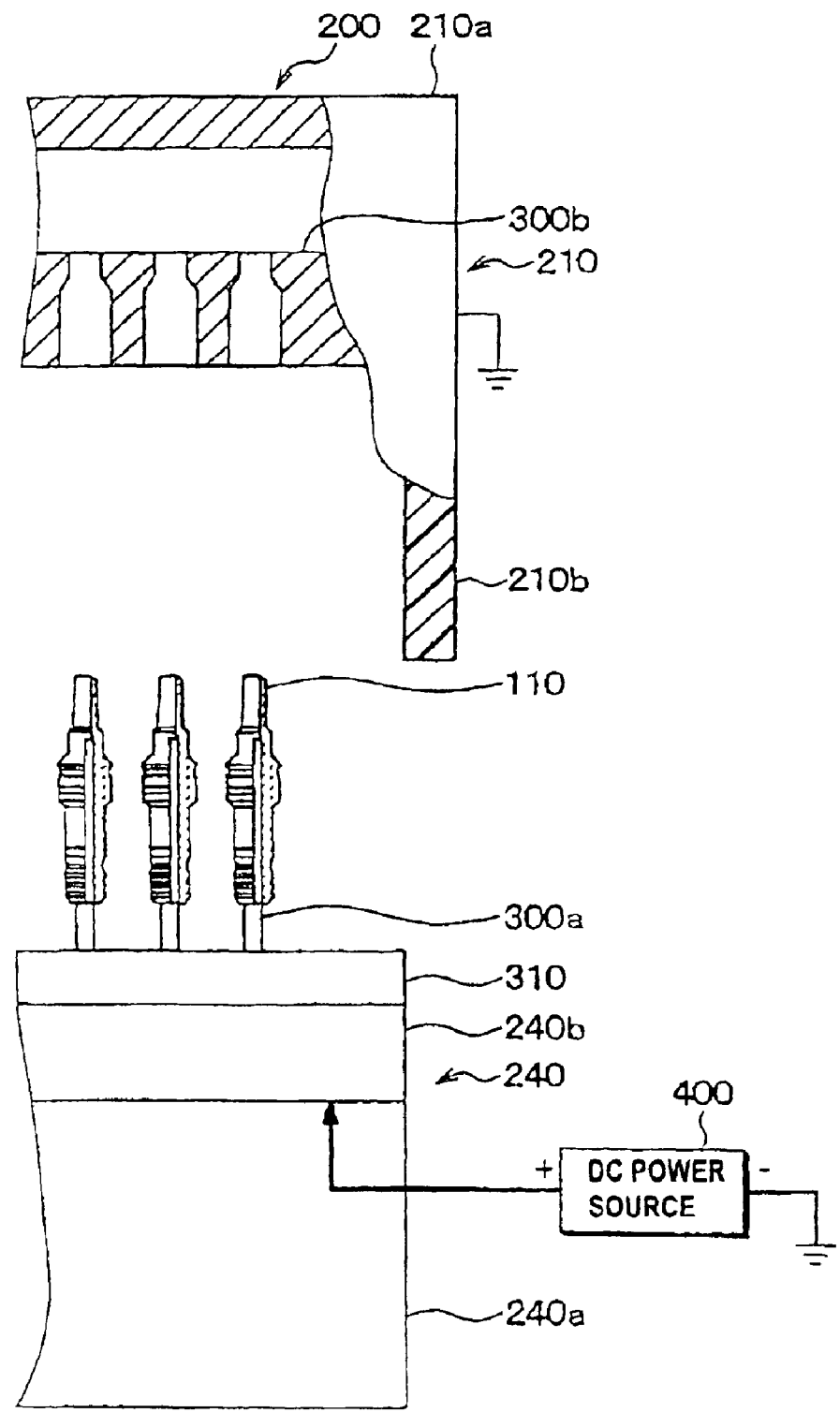
FIG. 2 shows the apparatus of FIG. 1, in a condition in which a movable portion of a pressure-proof chamber is in a raised position.

FIG. 2 shows the upper movable portion 210 raised to its highest position. Exchanging of a batch of insulators that have been inspected, for a new batch, is performed with the apparatus in the condition shown in FIG. 2.

The supporting portion 240 is formed of a support stage 240a, having mounted on its upper face a pedestal 240b, and a pallet 310 having a flat shape, which is disposed on the upper face of the pedestal 240b, with a plurality of first electrodes 300a being respectively fixedly attached to the pallet 310, extending upward from the top face of the pallet 310.

The support stage 240a is formed of an electrically insulating material, while the pedestal 240b, pallet 310 and first electrodes 300a are formed of metal and so are electrically conducting.

In this example (applied to spark plug insulators, having a central axially extending aperture which is of tapered shape) each of the first electrodes 300a is of elongated cylindrical shape, of appropriate diameter for insertion into the aperture of an insulator and for thereby supporting the insulator, and can for example be attached to the pallet 310 by screw attachment, i.e., with each pallet 310 having the lower end thereof formed with a screw thread, which engages in a threaded aperture in the pallet 310. There can for example be a total of 49 first electrodes 300a, arranged in a 7×7 array configuration. To simplify the drawings, only three of the pallet 310 are shown in FIGS. 1, 2.

In that way, each of the plurality of first electrodes 300a engages in the central aperture of a corresponding one of the batch of insulators 110 which are to be inspected, as illustrated in FIGS. 1, 2.

Each first electrode 300a is connected to the positive terminal of a DC power supply 400, via a connecting cable and a conductive path passing through the pedestal 240b and the pallet 310. The negative terminal of the DC power supply 400 is connected to ground potential, as is also a case portion 210a and the second electrode 300b (each of these being formed of metal).

The pallet 310 is set at a predetermined position on the top of the pedestal 240b by means of a raised peripheral portion of the top face of the pedestal 240b (not shown in the drawings). Thus, exchanging of a pallet 310 for a pallet which supports a new batch of insulators 110 can be easily and quickly performed, so that the inspection process can proceed smoothly.

As can be understood from FIGS. 1 and 2, the height at which each of the insulators 110 is supported above the top of the pallet 310 (and hence, the extent to which each insulators 110 is inserted into the corresponding aperture in the second electrode 300b, in the closed condition illustrated in FIG. 1) is determined by the length of each of the first electrodes 300a. Thus, by using pallets having respectively different lengths of the first electrodes 300a, it becomes possible to inspect insulators having various different sizes. That is to say, by selecting a pallet having first electrodes 300a of appropriate length, the inspection range for the insulators of a batch can be arbitrarily determined (where "inspection range" signifies the extent of the portion of each insulator that is actually subjected to inspection, i.e., the portion whose periphery becomes enclosed within an aperture of the second electrode 300b). Thus, the method can be flexibly applied to insulators of various different shapes and sizes, by selecting a pallet having first electrodes 300a of appropriate length (and/or of appropriate diameter, in accordance with the diameter of the central aperture in each insulator). Furthermore, depending upon the internal shape of the apertures in the insulators, the first electrodes might be formed in some configuration other than a straight cylindrical shape.

The upper movable portion 210 of the pressure-proof chamber 200 is formed of the aforementioned case portion 210a, an electrically insulated portion 210b, and the second electrode 300b.

When the upper movable portion 210 is moved to its lowermost position, the upper movable portion 210 hermetically seals the interior of the pressure-proof chamber 200. An air supply pipe (not shown in the drawings) is provided, extending from the exterior into the interior of the pressure-proof chamber 200, with that pipe being connected to an air compressor (not shown in the drawings) through a dehumidifier filter, to lower the humidity of the air which is pumped into the pressure-proof chamber 200. As a result, the pressure-proof chamber 200 becomes filled with dry air under a pressure which is higher than atmospheric pressure, when a flow of air is supplied from the compressor through the dehumidifier filter.

The pressure within the pressure-proof chamber 200 is preferably set to a maximum gauge value of 1 MPa.

The insulated portion 210b is formed with a layer of electrically insulating material such as epoxy-bonded glass fiber, to provide insulation between the upper movable portion 210 and the pallet 310, while also constituting a side wall portion of the pressure-proof chamber 200.

The second electrode 300b is formed of metal plate, with an array of apertures 900 formed therein as shown in FIG. 2, respectively positioned in accordance with the positions of corresponding ones of the array of first electrodes 300a. The respective sizes and positions of these apertures 900 are determined such that a portion of each of the insulators 110 will become peripherally enclosed within an aperture 900 when the upper movable portion 210 is brought to its lowermost position (shown in FIG. 1), while ensuring that the operation of lowering the upper movable portion 210 will not be obstructed due to contact between the insulators 110 and the second electrode 300b. The resultant condition is shown in FIG. 1, with each of the first electrodes 300a being located within the aperture of a corresponding one of the insulators 110, and each insulator 110 being peripherally enclosed by one of the apertures 900 in the second electrode 300b.

It thus becomes possible to inspect the entire periphery of each of the insulators 110, without requiring to rotate each insulator. Hence, it is made unnecessary to employ a rotational apparatus for rotating each of the insulators 110.

Furthermore, due to the fact that the second electrode 300b is formed of metal plate, the detection range (as defined hereinabove) can be increased as required, by increasing the thickness of the metal plate. Hence, there is a minimum of restriction placed upon determination of the detection range. That is to say, if the thickness of the metal plate is increased then there is a corresponding increase in the size of the area in which a potential difference is applied between the second electrode 300b and a first electrode 300a, so that there is a corresponding increase in the extent of the portion of an insulator 110 which is actually subjected to testing (by detection of the level of any leakage current which may flow through a defect in that portion of the insulator). Conversely, the detection range can be made more narrow by reducing the thickness of the metal plate which forms the second electrode 300b.

The apertures 900 formed in the second electrode 300b are shaped such as to match the outer shape of each of the insulators 110. Hence with this embodiment, applied to spark plug insulators, the diameter at the top of each aperture 900 in the second electrode 300b is made smaller than that at the lower part of each aperture. The second electrode 300b is attached by bolts (not shown in the drawings) to the inner side of the case portion 210a, in such a manner that the position in which the second electrode 300b is fixed can be adjusted upward or downward, if necessary, in order to be set to an appropriate position for inspection of a specific size of insulator. Alternatively, the second electrode 300b can be exchanged for a second electrode 300b having a different configuration (i.e., different diameter and/or shape of each of the apertures 900) if required, for the purpose of inspection of a specific size or shape of insulator. It can thus be understood that with the method of the present invention, using such a type of inspection apparatus, a wide range of various different shapes and sizes of insulators can be inspected, while in addition the detection range which is used in such an inspection can be arbitrarily set.

The DC power supply 400, whose positive terminal is connected to each of the first electrodes 300a and whose negative terminal is connected to the second electrode 300b, as described above, is preferably capable of being set to produce a potential difference of approximately 50 kV.

In addition, the DC power supply 400 is preferably configured such as to limit the maximum level of current which can flow between the first electrodes 300a and the second electrode 300b. The DC power supply 400 is provided with a circuit for measuring the level of current (i.e., leakage current) that flows between the first electrodes 300a and the second electrode 300b when the high potential difference is applied, and with a display device (not shown in the drawings) for displaying the level of leakage current.

The procedure for performing inspection with the above apparatus is as follows. Firstly, with the upper movable portion 210 in the raised position shown in FIG. 2, the first electrodes 300a are engaged in corresponding ones of a batch of insulators 110, so that the insulators 110 become supported in a vertically extending manner by the first electrodes 300a. The upper movable portion 210 is then moved to its lowest position (as shown in FIG. 1), then the air compressor (not shown in the drawings) is set in operation, to fill the interior of the pressure-proof chamber 200 with dry air under high pressure. The DC power supply 400 is then activated to apply a high potential difference (e.g., approximately 50 kV) between the first electrodes 300a and the 300b during a predetermined time interval. During that time interval, the level of leakage current which flows between the first electrodes 300a and second electrode 300b is measured. If that level of leakage current exceeds a predetermined threshold value, then it is judged that there is at least one defective insulator among the insulators 110. That is to say, if there is no defective insulator, then only a very low level of leakage current will flow over the surface or through the body of each of the insulators 110, so that the total level of leakage current which flows between the first electrodes 300a and the second electrode 300b will be below the threshold value. However if at least one of the insulators 110 is defective, then a level of leakage current will flow through such an insulator that is approximately ten times the value of the total leakage current which flows between the first electrodes 300a and the second electrode 300b when there no defect in any of the insulators. Hence, it is possible to reliably judge whether or not all of the insulators 110 are free from defects, based on the level of leakage current which is measured by the DC power supply 400.

If the aforementioned air compressor (not shown in the drawings) were not utilized, so that the above inspection procedure were performed with the interior of the pressure-proof chamber 200 at atmospheric pressure, then spark discharges would occur between the first electrodes 300a and second electrode 300b, with such spark discharges occurring at a level of potential difference as low as approximately 15 kV (depending upon the spacings between each of the first electrodes 300a and the second electrode 300b). Hence it would be impossible to apply the method of the present invention, whereby the level of leakage current is measured under a condition of very high voltage difference between the first electrodes 300a and the second electrode 300b.

However with the interior of the pressure-proof chamber 200 filled with dry air under a pressure that is higher than atmospheric pressure, providing a very high degree of electrical insulation, the occurrence of spark discharges between the first electrodes 300a and the second electrode 300b is suppressed, even with a potential difference as high as 50 kV applied. Hence, leakage current measurement can be reliably performed to ensure that each insulator which passes inspection will provide an extremely high degree of insulation.

If the leakage current that is measured for a batch of insulators by the inspection process described above does not exceed the predetermined threshold value, signifying that all of the insulators of that batch are free from defects, then that entire batch are outputted as items which have passed inspection. However if the leakage current that is measured by that concurrent batch defect inspection process is found to exceed the predetermined threshold value, then all of the insulators of that batch are successively subjected to an individual unit sorting inspection procedure.

Figure 3:
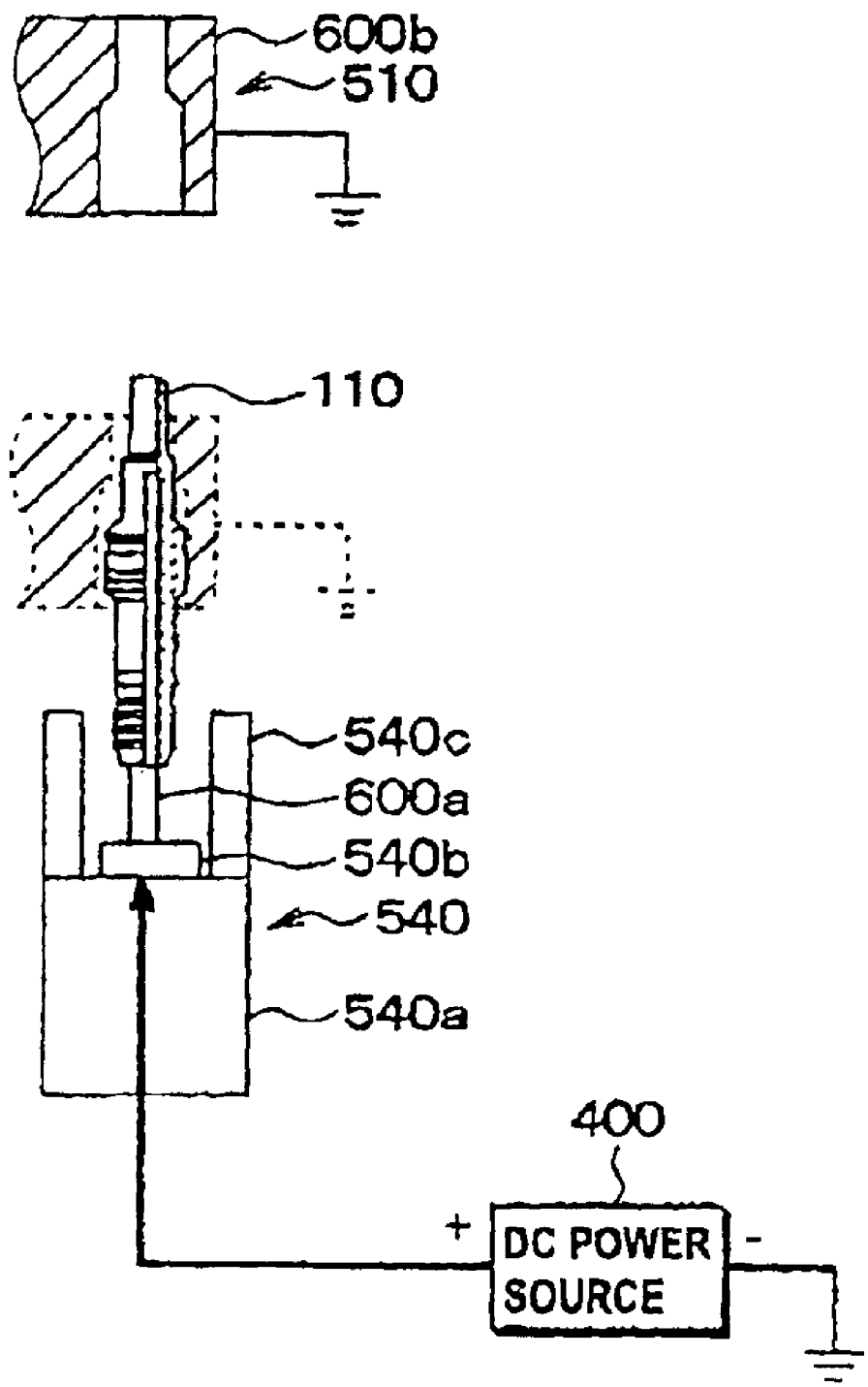
FIG. 3 is a partial diagram of an example of an apparatus for performing inspection of insulators as individual units, by detection of leakage current.

This individual unit sorting inspection procedure is performed using an apparatus configuration as illustrated in FIG. 3. In this case, instead of using the interior of the pressure-proof chamber 200, filled with dry air under a pressure that is higher than atmospheric pressure in order to apply a high value of test voltage to the electrodes, the individual unit sorting inspection is performed at atmospheric pressure. This is because, when an electrical discharge occurs via a defective portion of an insulator while the concurrent batch defect inspection procedure described above is being performed, that defective portion will become enlarged as a result of the electrical discharge. As a result, if such a defective insulator is then tested under atmospheric pressure, even when using a level of test voltage that is substantially lower than that which is used in the concurrent batch defect inspection process, an electrical discharge will take place via the defective portion.

The apparatus used in the individual unit sorting inspection procedure, shown in FIG. 3, consists of a supporting portion 540 formed of a supporting stage 540a, a pedestal 540b, and an insulating portion 540c, with a first electrode 600a being fixedly attached to the pedestal 540b as shown, and a movable upper portion 510 formed with an aperture 950 to constitute a second electrode 600b. The movable upper portion 510 can be moved between an upper position (shown by the full-line portions of FIG. 3) by a slide mechanism (not shown in the drawings), and a lower position in which inspection is performed.

The supporting stage 540a is formed of an electrically insulating material, with the pedestal 540b attached to the upper face thereof. The single first electrode 600a, having an elongated cylindrical configuration in this embodiment, is fixed to the pedestal 540b in a removably attached manner (e.g., by being screwed therein), extending vertically upward. Hence, electrodes 600a having various different lengths can be mounted, as required for a specific type of insulator. With the second electrode 600b in the lower position as indicated by the dotted-line portions of FIG. 3 (i.e., when the movable upper portion 510 is moved to its lowest position) and with an insulator 110 having the aforementioned central axially extending aperture thereof with the first electrode 600a engaged therein, a peripheral portion of the insulator 110 is enclosed by the aperture 950 of the second electrode 600b, with the extent of that portion (i.e., the detection range) being determined by the length of the first electrode 600a. Hence, in the same way as described for the apparatus of FIGS. 1, 2, the detection range that is used during inspection can be arbitrarily determined, for insulators that may be of various different lengths and shapes, by utilizing a first electrode 600a which is of appropriate length.

The portion 540c of the supporting portion 540 is formed of an electrically insulating material, and is disposed surrounding (and spaced apart from) the periphery of the first electrode 600a. The pedestal 540b is formed of metal and is connected by a cable to the positive terminal of the DC power supply 400 (whose negative terminal is connected to ground potential) so that the first electrode 600a is thereby connected to the positive terminal of the DC power supply 400. The second electrode 600b is formed of metal plate, of appropriate thickness, in the same way as described for the apparatus of FIGS. 1, 2 above, and is connected to ground potential, i.e., to the negative terminal of the DC power supply 400.

With this apparatus, in the same way as for the apparatus of FIGS. 1, 2, inspection of the insulators 110 can be performed around the entire periphery of the insulators 110, without the need to rotate the insulator, so that it is not necessary to provide a rotation apparatus for rotating the insulators 110.

By selecting various values of thickness of the metal plate which forms the second electrode 600b, the inspection range (as defined hereinabove) can be arbitrarily determined as appropriate for various different types of insulator, in addition to the aforementioned capability for determining the detection range by selective various different lengths of first electrode 600a. Furthermore, second electrodes 600b having various different sizes and shapes of aperture 950 may be utilized, as appropriate for various different sizes and configurations of insulator 110.

It can thus be understood that the apparatus and method used in the individual unit sorting inspection procedure provide the same advantages over the prior art as those of the concurrent batch defect inspection procedure, described above referring to FIGS. 1, 2, but with the individual unit sorting inspection being performed under a condition of atmospheric pressure, using a value of test voltage which can be substantially less than that used in the concurrent batch defect inspection procedure, and being applied to one insulator 110 at a time.

The overall processing flow used in this embodiment will be described referring to the flow diagram of FIG. 4. The defect rate of insulators 110, such as spark plug insulators, is extremely low, being of the order of approximately several ppm (parts per million). Hence, performing individual unit sorting inspection of all insulators is extremely time-consuming and inefficient. For that reason with the method of the present invention, two separate inspection procedures may be applied, as will be described referring to the flow diagram of FIG. 4.

Figure 4:
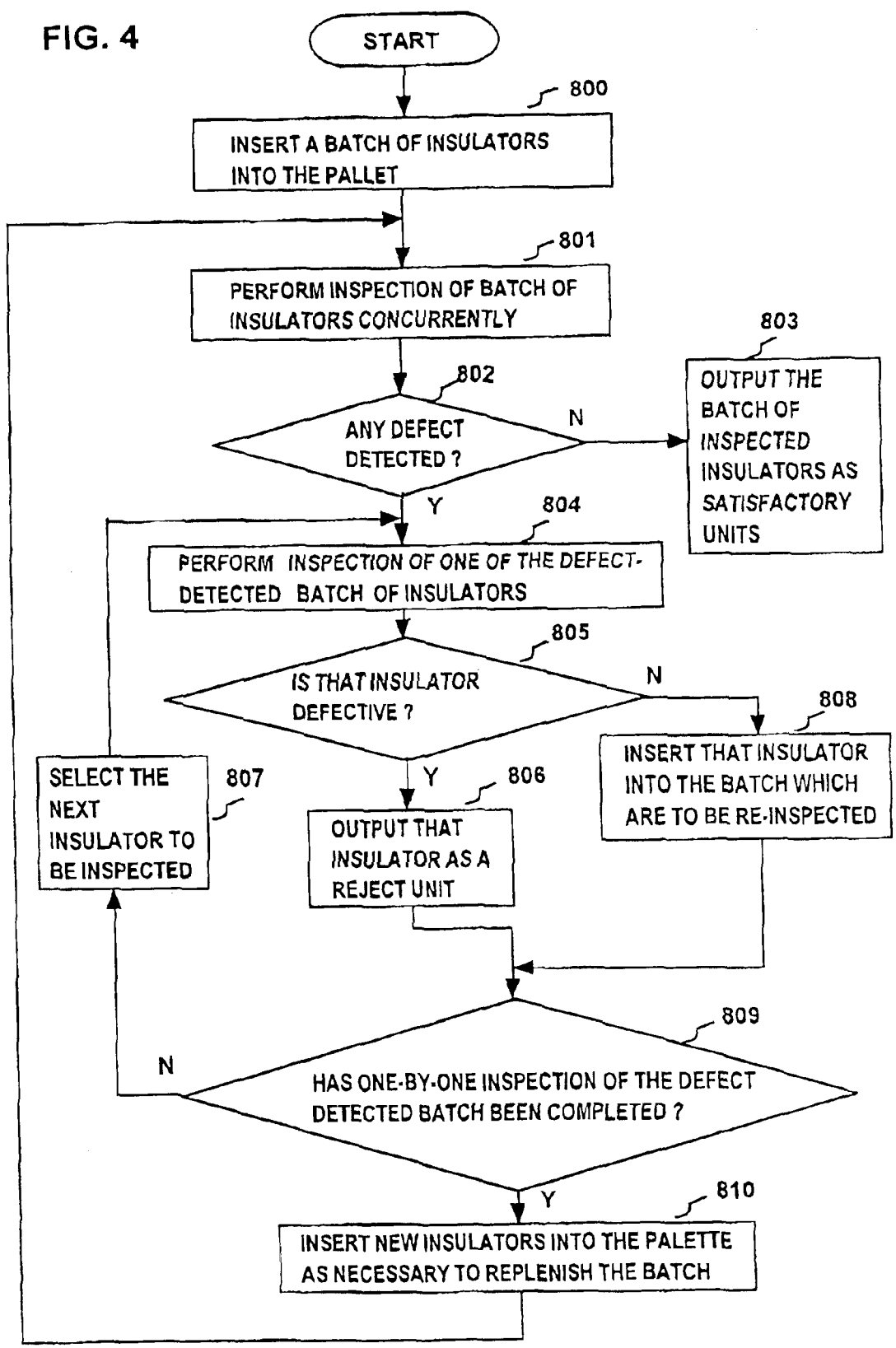
FIG. 4 is a flow diagram for describing a sequence of operations which implement a method of insulator defect inspection according to the present invention.

In FIG. 4, the steps 800, 801, 802 and 803 constitute a concurrent batch defect inspection procedure, which is applied to an entire batch of insulators, while the set of steps 804 to 810 constitute the individual unit sorting inspection procedure, which is applied successively to each of the insulators of a batch when a defect has been found by the concurrent batch defect inspection procedure. In that way, a high efficiency of inspection can be achieved, since if a batch of insulators contains not defects then that fact will be detected by a single inspection operation, and that entire batch then outputted as having passed inspection. However if at least one of the insulators of a batch has a defect, then that will be found by the concurrent batch defect inspection, and the specific insulator or insulators having the defect(s) will then be determined, and outputted as an item which has failed inspection, by means of the individual unit sorting inspection procedure.

In the flow diagram of FIG. 4, firstly in step 800 a pallet 310 has a new batch of insulators 110 (e.g., a total of 49 insulators) mounted on respective ones of the first electrodes 300*a* as described above, the upper movable portion 210 is raised to its upper position as shown in FIG. 2, and the pallet 310 is set at a predetermined position on the pedestal 240*b*. The upper movable portion 210 is then moved down to its lowermost position, as shown in FIG. 1, so that peripheral portions of the insulators 110 become enclosed within respective ones of the apertures 900 in the second electrode 300*b*. The aforementioned air compressor is then set in operation, to fill the interior of the pressure-proof chamber 200 with dry air at a predetermined pressure that is higher than atmospheric pressure.

Next (step 801) the output voltage of the DC power supply 400 is set at a high value (e.g., 50 kV) during a predetermined time interval. During that time, the level of leakage current that flows between the first electrodes 300*a* and the second electrode 300*b* is measured and displayed by the DC power supply 400, and the upper movable portion 210 is then raised back to its uppermost position as shown in FIG. 2. A decision is then made (step 802) as to whether or not there is any defect in the batch of insulators 110, in accordance with whether or not the level of leakage current exceeds a predetermined threshold value. If the leakage current does not exceed the threshold value, then this indicates that the entire batch of insulators 110 has passed inspection. However if the leakage current exceeds the predetermined threshold value, then the aforementioned individual unit sorting inspection is started, beginning with step 804, in which one of the insulators 110 is removed from the pallet 310 and is set on the first electrode 600*a* of the apparatus of FIG. 3, with the movable upper portion 510 at its uppermost position. The movable upper portion 510 is then set at its lower position, and that insulator 110 is then subjected to the individual unit inspection process described hereinabove referring to FIG. 3. A decision is made as to whether or not the insulator 110 has passed the single-unit inspection operation (step 805) based on whether the level of leakage current exceeds the aforementioned predetermined threshold value that is used in the individual unit sorting inspection procedure.

If the leakage current does not exceed that threshold value, then that insulator 110 is made part of a batch which will be again subjected to the concurrent batch defect inspection procedure (step 808). The reason for this is that the level of test voltage which is applied from the DC power supply 400 in the individual unit sorting inspection procedure is substantially lower than that which is used in the concurrent batch defect inspection procedure. Hence it is necessary to re-test an insulator at the higher value of test voltage, even if it has passed inspection at the lower value of test voltage.

If the leakage current exceeds the threshold value, then that insulator 110 is rejected as having failed the inspection (step 806).

A decision is made as to whether or not all of the batch of insulators have been subjected to the individual unit sorting inspection procedure (step 809) and if not, another of the insulators from the batch which failed the concurrent batch defect inspection procedure is set in the apparatus of FIG. 3 (step 807) and steps 804, 806 or 808, and 809 are repeated.

When all of the batch have been subjected to the individual unit sorting inspection procedure, then (step 810) one or more new insulators are added (i.e., to make up a full batch of 49 insulators) to the set of insulators that have been selected (in steps 805, 808) to be re-tested by the concurrent batch defect inspection procedure. The above process, starting from step 801, is then applied to this replenished batch of insulators 110.

The method of the present invention has been described in the above for the case of inspection of spark plug insulators prior to assembly of completed spark plugs. However it would be equally possible to apply the method to inspect the insulators of spark plugs after these have been assembled into complete units. In that case, the central electrode of each spark plug could be utilized to perform the functions of the first electrode 300*a* and first electrode 600*a* described above, and the ground electrode of the spark plug could be used as the second electrode 300*b* and as the second electrode 600*b*.

Furthermore in the above description of the individual unit sorting inspection procedure it is assumed that the inspection is performed at atmospheric pressure. However it would be equally possible to perform that inspection procedure within the pressure-proof chamber 200, filled with dry air under a pressure that is higher than atmospheric pressure. In that case, the individual unit sorting inspection procedure would constitute a final inspection of each insulator 110 on an individual basis, so that it would be unnecessary to again apply the concurrent batch defect inspection to those insulators which have passed the individual unit inspection.

Moreover in the above description, each of the second electrode 300*b* and second electrode 600*b* is formed of metal plate, with through-hole apertures in the metal plate accommodating respective insulators 110. However it is not essential to provide through-hole apertures, and it would be equally possible to provide cavities in second electrode 300*b* and in the second electrode 600*b* which do not constitute through-holes, and into which the respective insulators 110 could be inserted.

Moreover, rather than forming the second electrode 300*b* and the second electrode 600*b* of metal plate having apertures or cavities formed therein, it would be equally possible to form these of wire which is shaped such as to peripherally enclose the respective insulators 110.

It can thus be understood that although the invention has been described above referring to a specific embodiment, various changes and modifications could be envisaged which fall within the scope claimed for the invention.

What is claimed is:

1. A method of inspecting an insulator to detect defects, said insulator having an aperture formed therein, the method comprising:

placing said insulator inside a pressure-proof chamber, with a first electrode disposed within said aperture of said insulator and with a second electrode disposed at the exterior of said insulator, filling said pressure-proof chamber with air under a pressure which is higher than atmospheric pressure, establishing a potential difference between said first electrode and second electrode, and measuring a level of leakage current which flows between said first and second electrodes, and judging whether said leakage current exceeds a predetermined value, to thereby judge whether or not said insulator is defective.

2. A method of insulator defect inspection according to claim 1, wherein said insulator comprises a plurality of insulators having respective apertures formed therein and said first electrode comprises a plurality of first electrodes corresponding to respective ones of said plurality of insulators, wherein said potential difference is established between said second electrode and each of said plurality of first electrodes, and wherein it is judged that there is a defect in at least one of said plurality of insulators when said leakage current exceeds said predetermined value.

3. A method of insulator defect inspection comprising:

performing concurrent batch defect inspection of a plurality of insulators which have respective apertures formed therein, by disposing each of a plurality of first electrodes in an aperture of a corresponding one of said plurality of insulators, and disposing a second electrode such as to enclose respective peripheries of said plurality of insulators, with said plurality of first electrodes, said plurality of insulators and said second electrode being enclosed within a pressure-proof chamber, filling said pressure-proof chamber with air under a pressure which is higher than atmospheric pressure, establishing a potential difference between each of said plurality of first electrodes and said second electrodes, and measuring a level of leakage current which flows between said plurality of first electrodes and said second electrodes, judging that there is a defect in at least one of said plurality of insulators, when said leakage current exceeds a first predetermined value, and when it is found that there is a defect, performing an individual unit sorting inspection of each of said plurality of insulators by disposing a first electrode in said aperture of said each insulator, with a second electrode disposed to enclose a periphery of said each insulator, establishing a potential difference between said first electrode and second electrode and measuring a level of leakage current which flows between said first and second electrodes, and judging that there is a defect in said each insulator, when said level of leakage current exceeds a second predetermined value.

4. A method of insulator defect inspection according to claim 3, comprising upon completion of processing all of said plurality of insulators by said individual unit sorting inspection, selecting each of said plurality of insulators that have been found to be free from defect by said individual unit sorting inspection, and applying said concurrent batch defect inspection to all of said selected insulators.

5. A method of inspecting an insulator to detect defects, said insulator having an aperture formed therein, the method comprising:

placing said insulator inside a pressure-proof chamber, with a first electrode disposed within said aperture of said insulator and with a second electrode disposed at the exterior of said insulator, filling said pressure-proof chamber with air under a pressure which is higher than atmospheric pressure, establishing a potential difference between said first electrode and second electrode, and measuring a level of leakage current which flows between said first and second electrodes, and judging whether said leakage current exceeds a predetermined value, to thereby judge whether or not said insulator is defective, wherein said pressure-proof chamber is filled with dry air under said high pressure, having a dew point which is lower than a predetermined value.

6. A method of inspecting an insulator to detect defects, said insulator having an aperture formed therein, the method comprising:

placing the entire insulator inside a pressure-proof chamber, with a first electrode disposed within said aperture of said insulator and with a second electrode disposed at and spaced apart from the exterior of said insulator, filling said pressure-proof chamber with air under a pressure which a higher than atmospheric pressure, establishing a potential difference between said first electrode and second electrode, and measuring a level of leakage current which flows between said first and second electrodes, and judging whether said leakage current exceeds a predetermined value, to thereby judge whether or not said insulator is defective.

* * * * *